(12) United States Patent
Allen

(10) Patent No.: US 10,610,435 B2
(45) Date of Patent: Apr. 7, 2020

(54) SURGICAL TABLE CLADDING PROTECTIVE DEVICE

(71) Applicant: Robert Dan Allen, Newbury, OH (US)

(72) Inventor: Robert Dan Allen, Newbury, OH (US)

( * ) Notice: Subject to any disclaimer, the term of this patent is extended or adjusted under 35 U.S.C. 154(b) by 0 days.

(21) Appl. No.: 16/131,372

(22) Filed: Sep. 14, 2018

(65) Prior Publication Data
US 2019/0083344 A1   Mar. 21, 2019

Related U.S. Application Data

(60) Provisional application No. 62/558,948, filed on Sep. 15, 2017.

(51) Int. Cl.
| | | |
|---|---|---|
| *A61G 13/06* | (2006.01) | |
| *A61G 13/10* | (2006.01) | |
| *A61G 7/018* | (2006.01) | |
| *A61B 6/04* | (2006.01) | |

(52) U.S. Cl.
CPC ............ *A61G 13/06* (2013.01); *A61G 7/018* (2013.01); *A61G 13/101* (2013.01); *A61B 6/0407* (2013.01)

(58) Field of Classification Search
CPC ...................................... A61G 13/06
USPC .................................... 5/600, 611
See application file for complete search history.

(56) References Cited

U.S. PATENT DOCUMENTS

| | | | |
|---|---|---|---|
| 5,528,782 A * | 6/1996 | Pfeuffer ................. | A61G 13/02 108/147 |
| 6,240,585 B1 | 6/2001 | Reinke | |
| 9,233,042 B1 | 1/2016 | Freude | |
| 9,782,315 B2 | 10/2017 | Langford | |
| 2007/0107126 A1* | 5/2007 | Koch ..................... | A61G 13/02 5/600 |
| 2009/0321604 A1* | 12/2009 | Revenus ................ | A61G 13/06 248/354.1 |

* cited by examiner

*Primary Examiner* — Fredrick C Conley
(74) *Attorney, Agent, or Firm* — Pearne & Gordon LLP

(57) ABSTRACT

A cladding protection device is provided for protecting a height adjustment mechanism used to raise and lower the height of an operating room table. The cladding protection device includes a plurality of bodies seated upon the table base of the operating room table to surround a perimeter of the height adjustment mechanism to thereby inhibit contact with foreign objects. In one example, a complimentary coupler comprising a first coupler on one of the plurality of bodies removably engages a second coupler on another of the plurality of bodies to form the cladding protection device. In another example, a plurality of inwardly projecting stand-offs are located in close proximity with the perimeter of the height adjustment mechanism to inhibit directional movement of the cladding protection device.

20 Claims, 16 Drawing Sheets

SURGICAL TABLE CLADDING PROTECTIVE DEVICE

CROSS-REFERENCE TO RELATED APPLICATIONS

This application claims the benefit of U.S. Provisional Application No. 62/558,948 filed 15 Sep. 2017, the entire disclosure of which is hereby incorporated herein by reference.

FIELD OF THE INVENTION

The present application relates generally to a guard device for a surgical table. More particularly, the application relates to a protective device that guards and protects the cladding segments that conceal the height adjustment assembly used to raise and lower the surface of a surgical table by providing protection that surrounds the perimeter of the height adjust assembly.

BACKGROUND OF THE INVENTION

Operating rooms commonly utilize surgical tables that can be repositioned to ergonomically accommodate medical personnel (e.g. surgeons, anesthesiologists, nurses, etc.) performing a medical procedure on a patient. In some instances, the table repositioning mechanism affords medical personnel the flexibility to elevate, lower, or angularly adjust the position of the surgical table surface. More specifically, the mechanism used to reposition the surgical table surface is typically surrounded by a telescoping cladding assembly that is perpendicularly situated in between the surgical table base and the bottom of the surgical table surface. In the context of performing a surgical procedure, it is known for medical personnel to use the base platform of the surgical table to temporarily store items. In some instances, items placed onto the base platform are inadvertently moved against or placed too close to the cladding assembly when lowering or repositioning the table surface. During these instances, the placed items can become lodged beneath a lip of one or more of the segments of the telescoping cladding assembly, subsequently rendering the cladding assembly and surgical table inoperable. Furthermore, the integrity of the surgical table can be compromised requiring the medical institution to incur costs associated with loss of use including rental of a replacement table as well as repairing or purchasing a replacement surgical table.

It is an object of the present application to provide a cladding guard to surround and protect the entire perimeter of the cladding assembly while also maximizing the integrity and safety of the operating room environment. It is also an object of the present application to provide a cladding protection device, the design of which compliments the aesthetics of the surgical table. It is also an object of the present application to provide a cladding protection device, the design of which fixes the device to the surgical table without physically fastening the device to the surgical table.

It is to be understood that both the foregoing general description and the following detailed description present example and explanatory embodiments of the application, and are intended to provide an overview or framework for understanding the nature and character of the application as it is claimed. The accompanying drawings, photographs, and attachments are included to provide a further understanding of the application and are incorporated into and constitute a part of this specification. The drawings, photographs, and attachments illustrate various example embodiments of the application, and together with the description, serve to explain the principles and operations of the application.

BRIEF SUMMARY OF THE INVENTION

The following presents a simplified summary of example embodiments of the invention. This summary is not intended to identify critical elements or to delineate the scope of the invention.

In accordance with one aspect, a cladding protection device is provided for protecting a vertically extending height adjustment mechanism used to raise and lower the height of an operating room table relative to a horizontal table base. The cladding protection device comprising a plurality of bodies seated upon said table base of said operating room table, each of said plurality of bodies comprising at least one side wall portion extending at least partially along a perimeter of said height adjustment mechanism. A complimentary coupler comprises a first coupler on one of said plurality of bodies and a second coupler on another of said plurality of bodies, such that when the first and second couplers are engaged together the plurality of bodies form the cladding protection device. When the first and second couplers are disengaged the plurality of bodies are separable from each other. In an installed state the cladding protection device surrounds said perimeter of said height adjustment mechanism to thereby inhibit foreign objects from contacting said height adjustment mechanism.

In accordance with another aspect, a cladding protection device is provided for protecting a vertically extending height adjustment mechanism used to raise and lower the height of an operating room table relative to a horizontal table base. The cladding protection device comprises a plurality of bodies seated upon said table base of said operating room table, each of said plurality of bodies comprising at least one side wall portion extending at least partially along a perimeter of said height adjustment mechanism. The plurality of bodies are adapted to be removably connected together to form the cladding protection device. A plurality of inwardly projecting stand-offs are located in close proximity with said perimeter of said height adjustment mechanism to inhibit directional movement of the cladding protection device when in an installed state around said height adjustment mechanism. At least one sidewall of each of the plurality of bodies comprises at least one stand-off. In the installed state the cladding protection device surrounds said perimeter of said height adjustment mechanism to thereby inhibit foreign objects from contacting said height adjustment mechanism.

BRIEF DESCRIPTION OF THE DRAWINGS

The foregoing and other aspects of the present invention will become apparent to those skilled in the art to which the present invention relates upon reading the following description with reference to the accompanying drawings, in which.

DESCRIPTION OF EXAMPLE EMBODIMENTS

Figure 1:
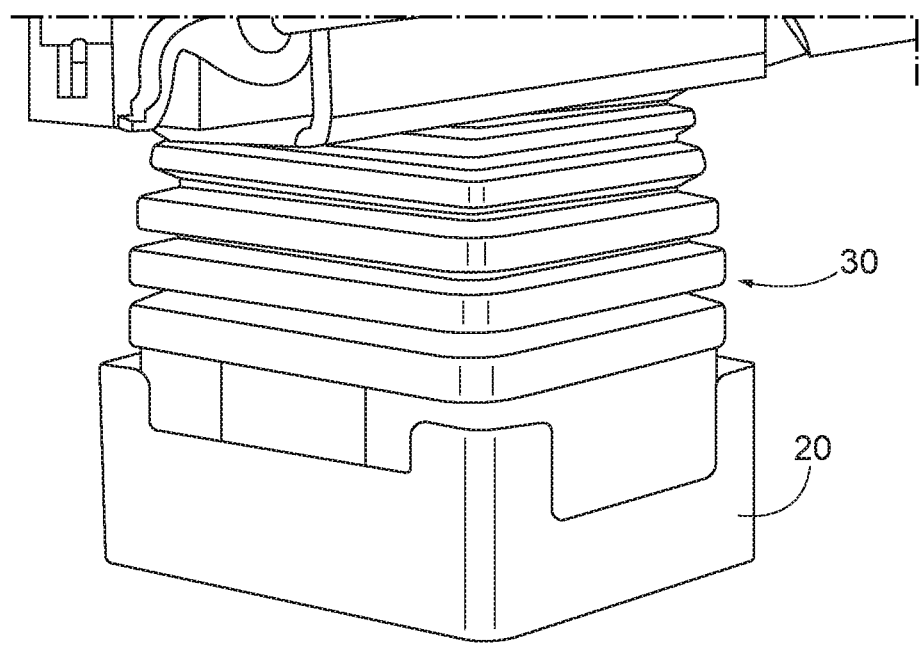
FIG. 1 illustrates a perspective view of an example surround cladding protection device as it is assembled around the pedestal base of a surgical table.

Example embodiments are described and illustrated in the drawings. These illustrated examples are not intended to be a limitation on the present invention. For example, one or more aspects can be utilized in other embodiments and even other types of devices. Moreover, certain terminology is used herein for convenience only and is not to be taken as a limitation. Still further, in the drawings, the same reference numerals are employed for designating the same elements.

Figure 2:
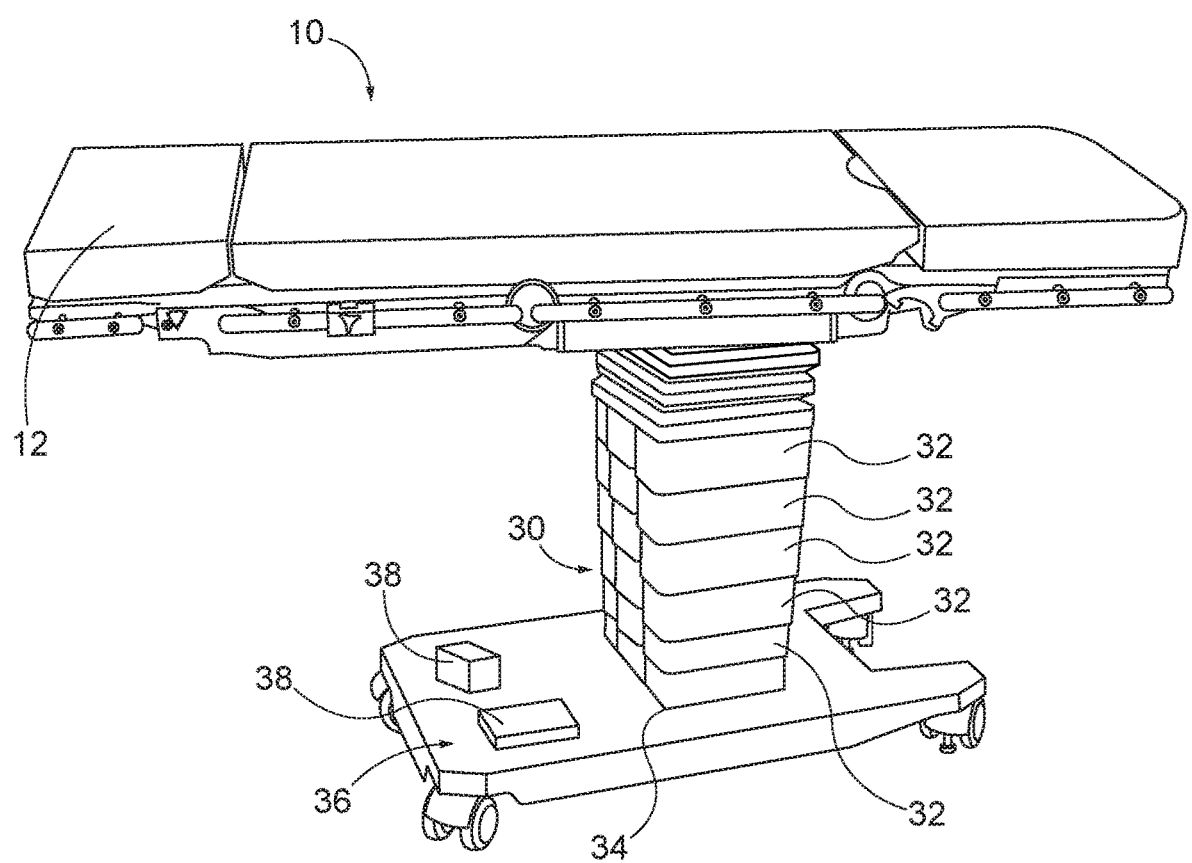
FIG. 2 illustrates a perspective view of an example surgical table with foreign objects stored on the base surface.

Turning to the shown example of FIG. 1, the present application relates generally to a surround cladding protection device 20 for protecting the height adjustment mechanism, such as the telescoping shroud, used to raise and lower the height of an operating room table 10. As shown in FIGS. 1-2, one example surgical table 10 is shown, although it is understood that the instant application could be used with any surgical table. The surgical table 10 includes a patient table surface 12 that is supported upon a table base surface 36 by a height adjustment mechanism. The table base is supported upon a support surface, such as a ground surface. The height adjustment mechanism is used to adjust the height of the patient table surface 12 relative to the table base surface 36 and the ground surface.

A movable shroud surrounds and protects the height adjustment mechanism. Often, the movable shroud has a telescoping design, such as a telescoping column that has several layers (usually 4 to 7 layers) depending on the manufacturer, although various other configurations are contemplated, such as a flexible accordion design, etc. The cladding protection device 20 is designed to be secured around the lower perimeter of the pedestal base 34 (see FIG. 2) of the height adjustment mechanism of a surgical table 10. The surround cladding protection device 20 is intended to surround and protect the perimeter of the cladding assembly 30 of the height adjustment mechanism from making contact with foreign objects 38 stored on the base surface 36 of the surgical table 10. Preferably, the cladding protection device 20 surrounds and circumscribes the entire perimeter of the cladding assembly 30 of the height adjustment mechanism, although optionally, it is contemplated that the cladding protection device 20 may protect less than the entire perimeter of the height adjustment mechanism. Additionally, the cladding protection device 20 is intended to protect only a predetermined vertical distance of the height adjustment mechanism, such as up to about 12 inches relative to the base surface 36, although the cladding protection device 20 could extend vertically more or less. More traditionally, the cladding assembly 30 is comprised of telescoping stainless steel shroud 32 members that are vertically movable during the upward and downward repositioning of the surgical table surface 12. The cladding assembly 30 is functionally suited to enclose, protect, and maintain the integrity of the internal mechanism (e.g. electronic and mechanical controls) used to elevate, lower, or angularly reposition the table surface 12.

Figure 3:
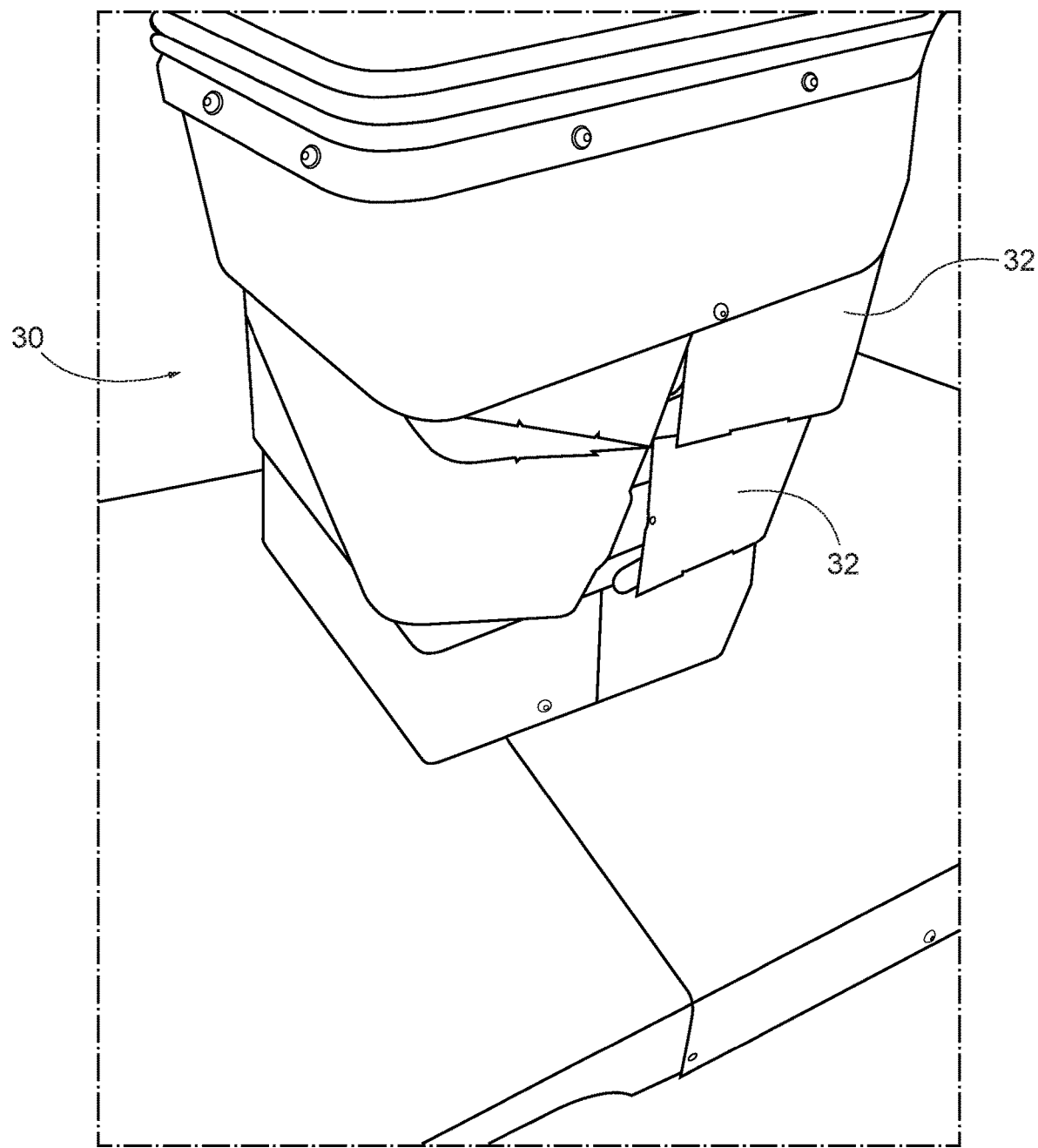
FIG. 3 illustrates a damaged surgical table cladding assembly.

Within the context of an operating room, it is presently known for medical personnel (e.g. anesthesiologists, nurses, surgeons, etc.) to store foreign objects 38 (e.g., SDC Machines, Arm Boards, Clark Sockets, Rail Clamps, etc.) onto the base surface 36 of the surgical table 10 prior to and/or during a medical procedure. During surgery, items or objects 38 are often placed on the table base 36 near the shroud 32, and often times things shift on the table base 36. As a result, it is common for the stored items or objects 38 to contact the telescoping shroud 32, especially during movement of the height adjustment mechanism, which damages the shroud 32. For example, the said objects 38 can make contact with the cladding assembly 30 and in doing so may become lodged beneath a lip of a telescoping shroud member 32, resulting in damage (see FIG. 3) to the cladding assembly 30 when the surgical table surface 12 is (lowered) repositioned. When this happens, the damage could render the surgical table 10 inoperable (e.g., the height adjustment mechanism is non-functional because the shroud is bent and cannot move up or down and/or the electronic controls and/or computer components of the table that are located inside the shroud can be damaged), and can consequently compromise the safety of the patient if it is required that they be transferred to another surgical table to complete a surgical procedure. Sterility may also be compromised.

In order to avoid such damage to the height adjustment mechanism, the surround cladding protection device 20 of the instant application has been invented. When the multiple piece cladding protection device 20 device is assembled, it acts to keep table accessories and other devices from coming into contact with the support column cladding (shrouds). Although the term cladding is used, it is contemplated that this includes telescoping cladding members or a flexible accordion shroud. That is, in an installed state the cladding protection device surrounds said perimeter of said height adjustment mechanism to thereby inhibit foreign objects from contacting said height adjustment mechanism. When disassembled the entire support column is exposed for cleaning, maintenance or repair.

Figure 4A:
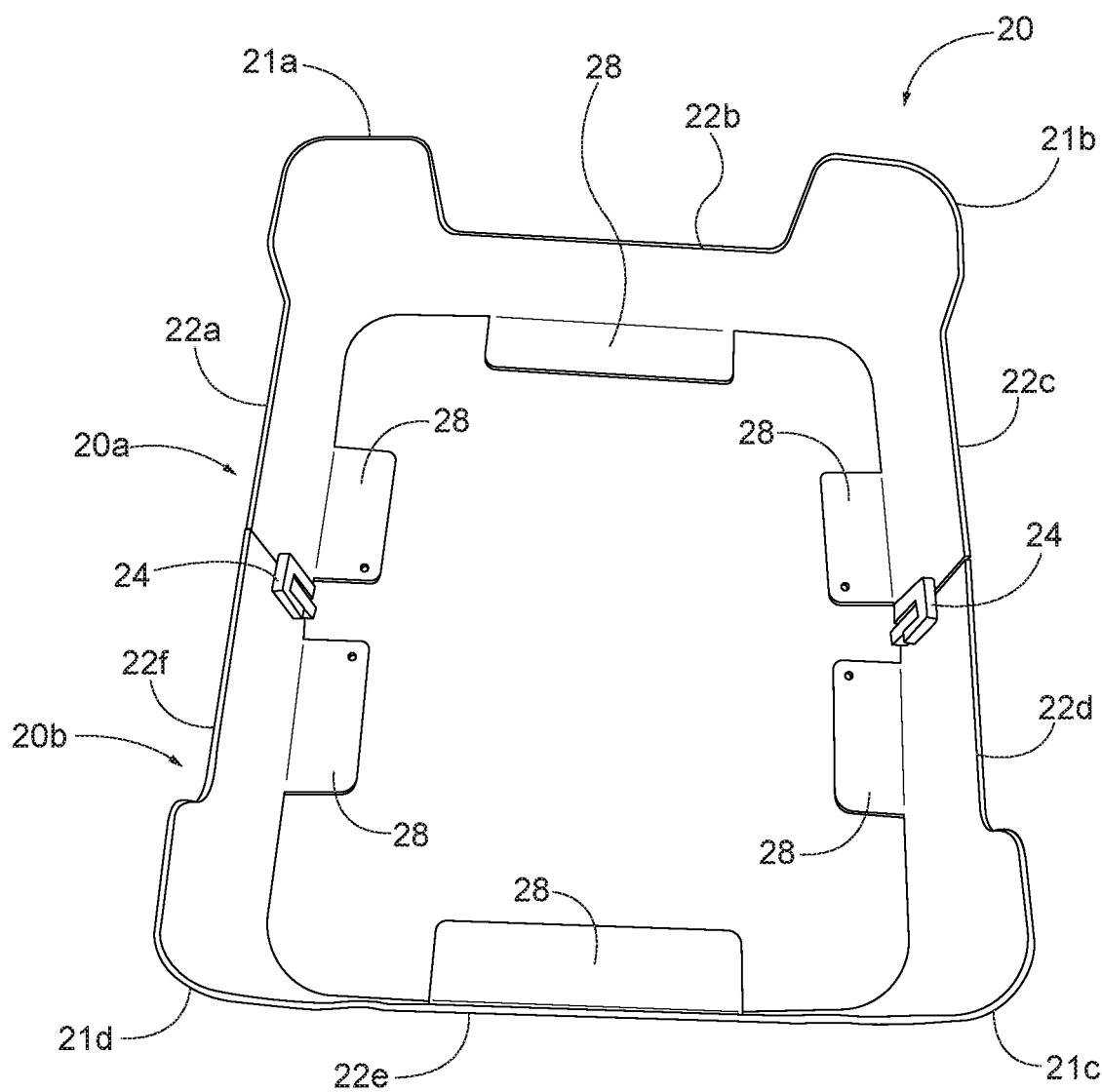
FIG. 4A illustrates a top view of the example surround cladding protection device.

In one embodiment, shown in FIG. 4A, the surround cladding protection device 20 is comprised of a plurality of separate bodies, such as a pair, comprising a first body 20a and second body 20b that are seated upon the table base of the operating room table and can be removably coupled together to form the completed surround cladding protection device 20. It is also contemplated that the cladding protection device 20 can be formed from three or more bodies. In the shown example, the two bodies 20a and 20b are presented as symmetrical halves. However, other configurations are also contemplated, and the bodies need not be symmetrical. In another example, a pair of side wall portions can define upwardly protruding corner 21a-d that has an increased height with respect to the nominal height of the side wall portions 22a-f of bodies 20a and 20b. Alternatively, the bodies 20a and 20b could include side wall portions 22a-22f having equal height dimensions to that of the corners 21a-21d, etc. Preferably, the corners 21a-21d are curved to avoid snagging against clothing, surgical drapes, cables, etc.

Figure 4B:
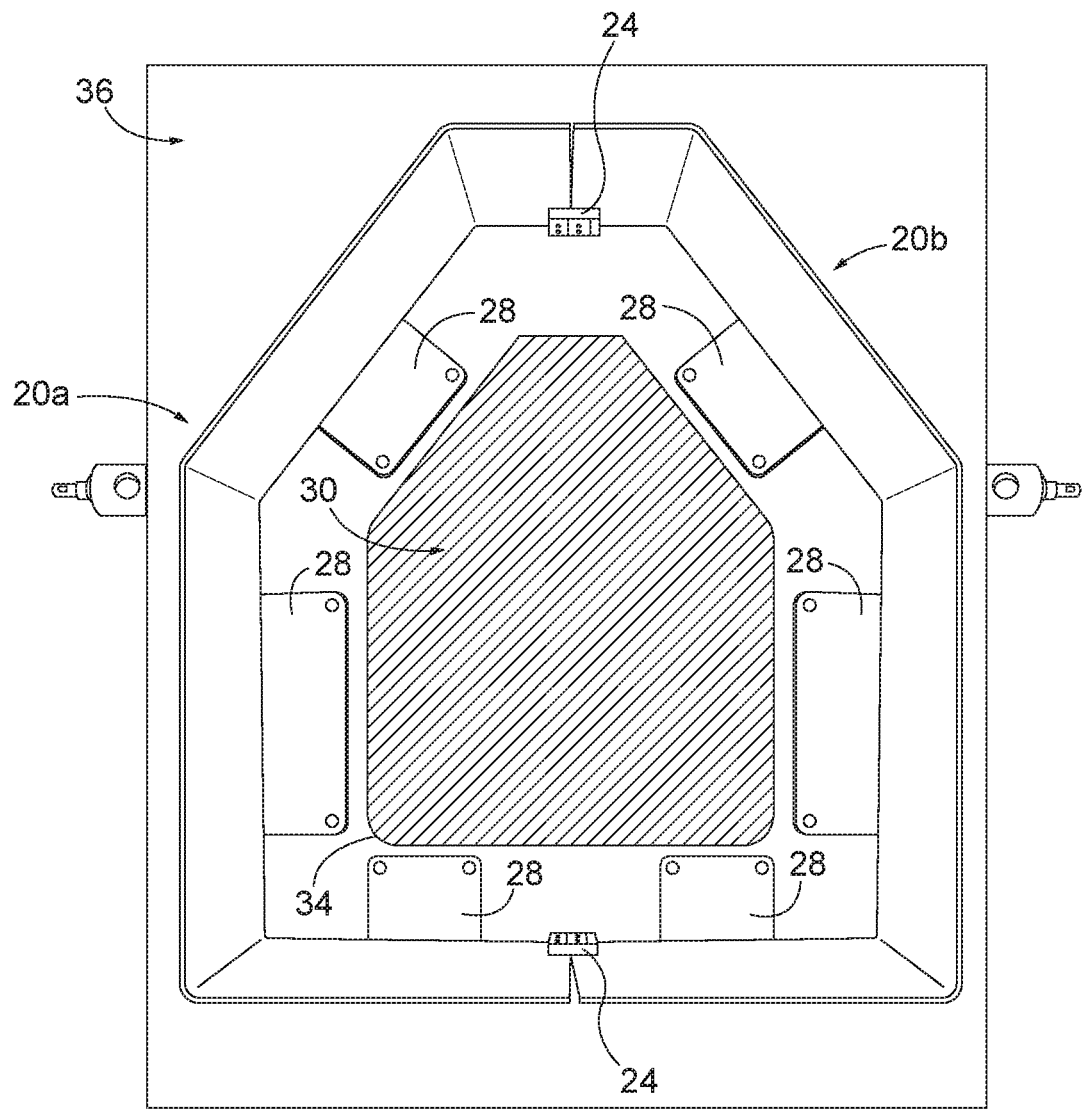
FIG. 4B illustrates a top view of another embodiment of the surround cladding protection device in an installed position.

FIG. 4B illustrates another embodiment of the surround cladding protection device 20 that is also comprised of two separate bodies 20a and 20b that can be removably coupled together to form the completed surround cladding protection device 20. Preferably, the cladding protection device 20 is maintained upon said table base by gravity without the use of fasteners.

Figure 5:
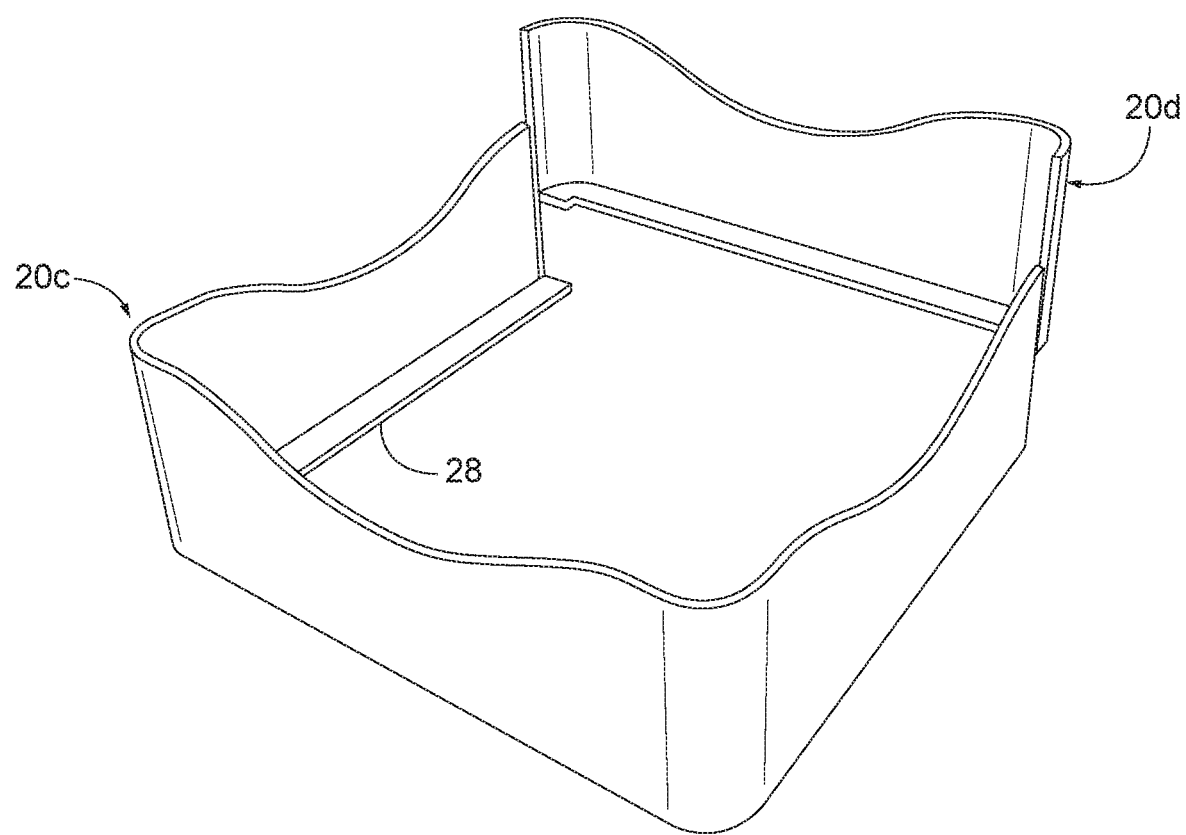
FIG. 5 illustrates a perspective view of another example of a surround cladding protection device.

In another embodiment as shown in FIG. 5, the surround cladding protection device 20 can comprise an integrally formed larger section 20c and a single end cap wall 20d. In another aspect (not shown), the surround cladding protection device 20 can be comprised of a plurality of wall and corner components that can be removably coupled together so as to accommodate a variety of pedestal base 34 designs. Additionally, the surround cladding protection device 20 could comprise various shapes and sizes. In this aspect, one could envision an asymmetric, square, circular, or oval-shaped design rather than the rectangular-shaped design shown in FIG. 4A or the truncated-pentagon or hexagon shape of FIG. 4B.

In another example, the side walls portions 22a-22f could feature outwardly facing storage compartments (not shown) situated on the outside perimeter of the surround cladding protection device 20 affording medical personnel the benefit of storing medical items during a medical procedure without concern that the stored items would damage the cladding assembly 30. In this way, one could envision hangers or other connector mechanisms (not shown) situated on the side or upper ridge of side wall portions 22a-22f designed to accommodate attached or hanging storage bins situated on the outside perimeter and below the top of the side wall portions 22a-22f of the surround cladding protection device 20.

Returning to FIG. 4A or 4B, the two bodies 20a and 20b can be made from a rigid material suitable for a surgical operating room environment (e.g. stainless steel, aluminum, or plastic, etc.), and may or may not be radiolucent. The cladding protection device 20 may be opaque, translucent, or transparent. In one example, the cladding protection device 20 can be made of transparent plastic (such as Plexiglas or the like) so that the operating room table height adjustment mechanism (and any indicia thereon) is readily visible therethrough. The cladding protection device 20 may be colored, and/or may include various indicia thereon (such as instructions, warnings, or the like).

Figure 6A:
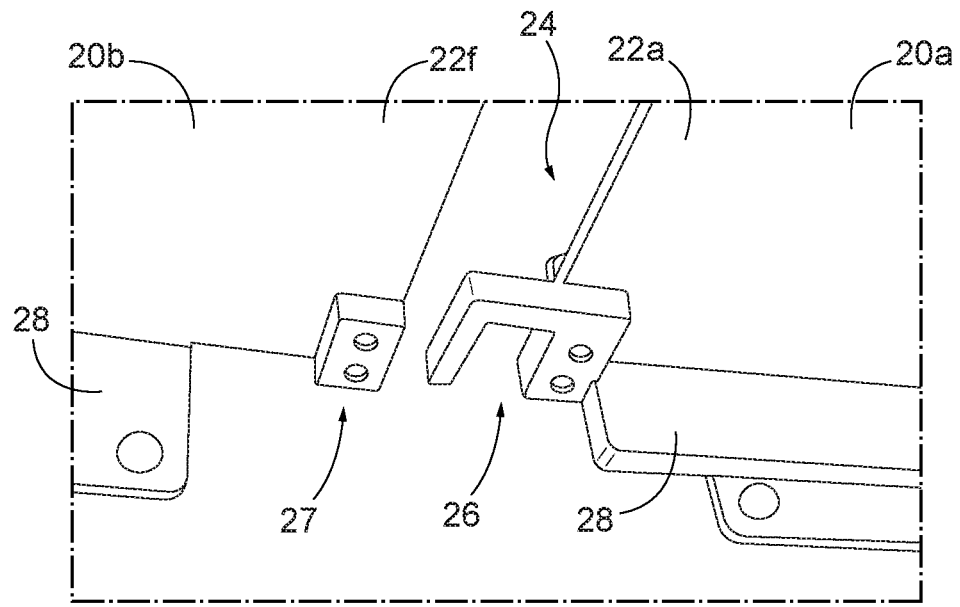
FIGS. 6A-6B show one example of complimentary couplers suited to join bodies of the surround cladding protection device together.
Figure 6B:
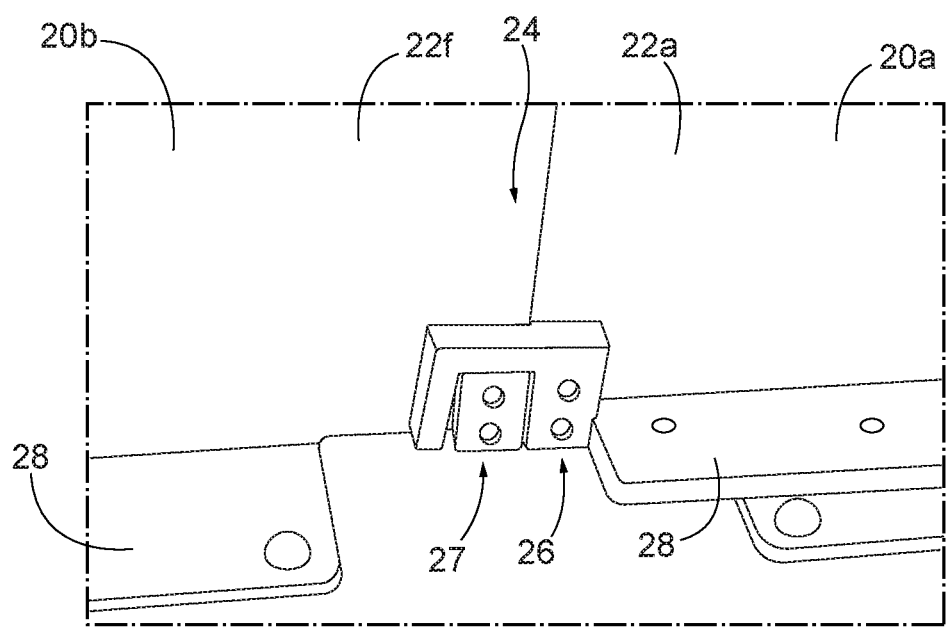

The bodies 20a and 20b can be removably coupled together through the utilization of complimentary couplers 24, such as a first coupler and a second coupler, although various numbers of couplers can be used. Turning to FIGS. 6A-6B, one example of the complimentary couplers 24 will be described. When the complimentary couplers 24 are engaged together, the bodies 20a, 20b are secured together to form the cladding protection device 20. This secure condition maintains the cladding protection device 20 around the operating room shroud 32. When the complimentary couplers 24 are disengaged from each other, the bodies 20a, 20b are unsecured and able to be separated. As shown, the complimentary couplers 24 are comprised of a U-shaped hook 26 and an elongated I-shaped catch 27 that is sized and shaped to fit into the open recess or space of the U-shaped hook 26. As shown in the Figures, the U-shaped hook 26 can be oriented as an inverted U-shaped hook 26 with the open recess or space facing downwards (in the installed position), although it is to be appreciated that the U-shaped hook 26 can be oriented variously to receive the catch 27, such as with the open recess or space facing upwards (in the installed position) or at an angled orientation. FIG. 6A shows the hook 26 and catch 27 separated, while FIG. 6B shows the catch 27 captured within the hook 26. The hook 26 extends from side wall portion 22a, and the catch 27 extends from side wall portion 22f. Alternatively, one could visualize the utilization of complimentary couplers 24 of various shapes, sizes, and varieties (e.g. magnetic, elastic members, snap, clasp, hook and eye type, etc.). Preferably, the hook 26 and catch 27 are located on the interior surface of the side wall portions, although the complimentary couplers 24 could also be positioned on the outer walls (not shown) in another embodiment.

To secure the bodies 20a and 20b together around the pedestal base 34, the hook 26 is seated onto the outer perimeter of the catch 27 and is secured in place by gravity. Alternatively, the catch 27 could be seated within the hook 26 recess or open space and held there by gravity. With the hook 26 seated onto the catch 27, the two bodies 20a and 20b form the surround cladding protection device 20 (FIG. 1) that is secured in place around the pedestal 34 by gravity. The hook 26 and/or catch 27 could also be retained together via clips, clasps, an interlocking structure, a tight tolerance or interference fit, or by other mechanical fasteners, etc.

In minimizing manufacturing costs, it can be appreciated that each of the separate bodies 20a and 20b can be formed from a single design whereby each body 20a and 20b includes a hook 26 and a catch 27 to reduce the engineering bill of materials for bodies 20a and 20b. The bodies 20a, 20b can be symmetrical, or different. For example, a hook 26 can be located on side wall portions 22a and/or 22d (see FIG. 4A), and a catch 27 can be located on side wall portions 22c and/or 22f. In this way, a single design could be manufactured, and the completed surround cladding protection device 20 can be formed by connecting the two bodies 20a and 20b together in a mirror arrangement. Alternatively, the hooks 26 can be located on a single body 20a (i.e, on side wall portions 22a and/or 22c) while the catches 27 can likewise be located on a single body 20b (i.e, on side wall portions 22d and/or 22f).

In another example, the hook 26 and/or catch 27 can include a corresponding bump or projection that can be received in a complimentary recess or hole of the other in a snap-fit or click-in manner. Additionally, the catch 27 is preferably located at a terminal edge of the wall portion, or set a short distance away from the terminal edge, so that when the complimentary couplers are engaged a close and tight fit can be provided between the terminal edges of the opposing wall portions of the bodies 20*a* and 20*b* when they are connected together to form the cladding protection device 20.

To additionally maintain and secure the cladding protection device 20 around the pedestal base 34 of the height adjustment mechanism, the bodies 20*a* and 20*b* can be provided with one or more discrete inwardly projecting stand-offs 28, which can be inwardly extending lips, flanges, or projections (see FIGS. 4A and 4B) that act as spacer partitions in close proximity with (i.e., immediately adjacent to or in contact with) the outer surface of the base of the pedestal base 34 to inhibit directional movement of the surround cladding protection device 20 when it is assembled around the pedestal base 34. Each of FIGS. 4A and 4B illustrate six projecting stand-offs 28 (i.e., three per each body 20*a* and 20*b*), although it is contemplated that more or less can be utilized. In one embodiment, where the perimeter of the height adjustment mechanism is defined by N walls, then the cladding protection device can comprises at least N side wall portions (i.e., an equal or greater number). For example, as illustrated in FIGS. 1 and 4A, the rectangular-shaped perimeter of the height adjustment mechanism is defined by 4 walls, and the cladding protection device 20 has at least 4 stand-offs 28 (i.e., 6 are shown). In another example, as illustrated in FIG. 4B, the hexagon-shaped perimeter of the height adjustment mechanism is defined by 6 walls, and the cladding protection device 20 has at least 6 stand-offs 28. It is noted that in the example of FIG. 4B, one side wall (i.e., the top-most wall, as shown) does not have a stand-off, and the corresponding wall of the height adjustment mechanism is free of a stand-off. Preferably, at least one stand-off is provided for most or all of the walls of the height adjustment mechanism, although this is not required and some walls may be devoid of an associated stand-off.

As further shown in FIG. 4B, the projecting stand-offs 28 are located at spaced locations around the exterior surface of the surgical table cladding assembly 30 at the pedestal base 34 to correspond to some, or possibly all, of the outside perimeter of the pedestal base 34. However, as also shown in FIG. 4B, not every side wall portion necessarily includes a stand-off; for example, as shown, only five of the six side wall portions include at least one stand-off. Various designs are contemplated based upon the size and geometry of the height adjustment mechanism perimeter. The leading edges of the projecting stand-offs 28 are in very close proximity to, or even in abutment with, the height adjustment mechanism (e.g., the base 34 of the surgical table support column and the shroud 32 members). The purpose of the projecting stand-offs 28 is to utilize the length of the tabs and their close proximity to the base of the support column in order to stabilize the surround cladding protection device 20 to prevent movement or removal thereof from the height adjustment mechanism in all required directions on the horizontal plane without having to physically affix the device to the surgical table base or the surgical table support column.

It is further appreciated that the fit between the inwardly projecting stand-offs 28 and the exterior surface of the surgical table cladding assembly 30 makes the cladding protection device 20 self-aligning. Each projecting stand-off 28 can be substantially flat and generally parallel to the surface of the table base 36, or can include a geometry corresponding to the table base 36, such as an L-shaped geometry relative to the side wall portions 22*a*-22*f*, curved or angled geometries, etc. It is to be appreciated that the table base 36 may have a varying geometry across its length or width, and so each stand-off 28 may only be parallel to the portion of the table base 36 that it rest upon or covers. Additionally, as shown in a comparison between FIGS. 4A and 4B, the projecting stand-offs 28 can be positioned according to the outer geometry of the pedestal base 34 so as to provide a matching fit. It is further contemplated that some or all of the projecting stand-offs 28 can be provided with a non-abrasive cushion or stabilizer (e.g., rubber, foam, etc.) on the bottom side thereof that contacts the table base 36 to avoid scratching or other damage to the operating room table 10.

Preferably, the stand-offs 28 are integral with the side wall portions of each body 20*a*, 20*b*. For example, the stand-offs 28 can each be formed together with a side wall, such as from a single sheet of material, and can be bent to the desired angle during manufacturing to provide the desired geometry. Similarly, if the cladding protection device 20 is made from a plastic material, the stand-offs 28 can be integrally molded together with the associated side walls. In one example, the stand-offs 28 can be arranged generally perpendicular to the side wall portion that it is connected to. Alternatively, the stand-offs 28 can be manufactured separately from the bodies 20*a*, 20*b* and can be separately secured thereto, preferably in a non-removable manner (mechanical fasteners, adhesives, welding, etc.). Various designs and combinations of the stand-offs 28 are contemplated.

As can be appreciated, various configurations of inwardly projecting stand-offs can be made available to accommodate varying types of pedestal base 34 and surgical table 10 designs. For instance, the inwardly projecting stand-offs 28 can represent one seamless stand-off 28 (see FIG. 5), or possibly a limited number of discrete, large or extended length stand-offs, protruding inwards from the walls of the surround cladding protection device 20. In some of the illustrated embodiments, each stand-off can have a length less than the respective side wall portion that it attached to. Alternatively, some or all of the stand-offs 28 can have a length similar or even equal to the length of the respective side wall portion that it attached to. Furthermore, the inwardly projecting stand-offs 28 can represent vertical ribs (not shown), designed to be situated underneath the lowest lip of a stationary shroud member 32.

Preferably, the cladding protection device 20 is maintained upon the operating room table via engagement of the projecting stand-offs 28 immediately adjacent to or against the cladding assembly 30. However, it is optionally contemplated in another example that the inwardly projecting stand-offs 28 can be removably secured to the base surface 36 with mechanical fasteners (e.g. screws, nuts, bolts, etc.) that can be inserted through holes (not shown) that are pre-formed (e.g. punched, drilled, cored, etc.) through the inwardly projecting stand-offs 28. In this way, the fasteners can be inserted through the holes and further inserted into the base surface 36 to secure the surround cladding protection device 20 to the base surface 36.

Figure 7:
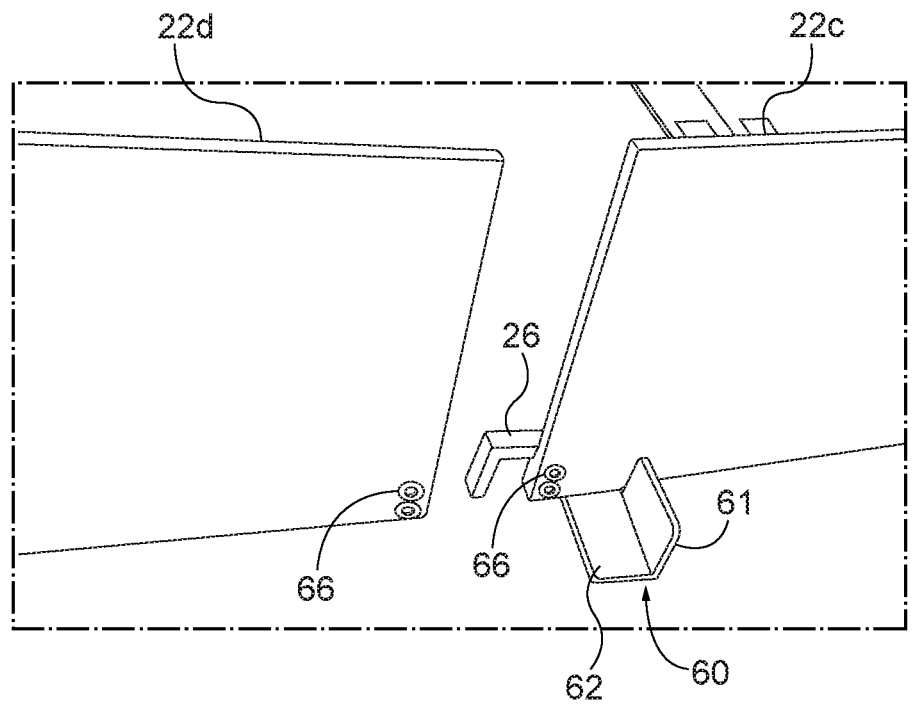
FIG. 7 shows an example moveable locking device used to retain the complimentary couplers together, where the moveable locking device is in an unlocked position.
Figure 8:
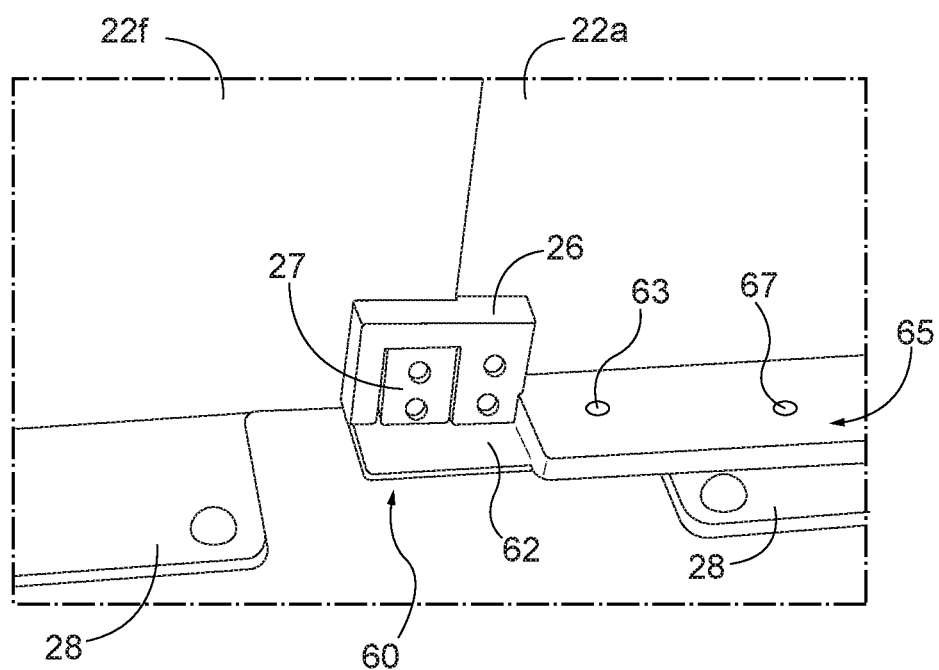
FIG. 8 is similar to FIG. 7, but shows the moveable locking device in a locked position.

In another aspect as shown in FIGS. 7-12, several example embodiments of a moveable locking device 60 can be utilized so as to prevent an inadvertent outwards movement of the hook 26 from the catch 27 to inhibit or prevent separation and removal of the cladding protection device 20. In the shown examples, the moveable locking device 60 can prevent an inadvertent upwards movement of the hook 26 from the catch 27 (with an inverted U-shaped hook), although alternatively, it could prevent downwards movement of the hook 26 from the catch 27 (with an upright U-shaped hook). In the Figures, this is illustrated as a pivoting/rotating wing-lock device, although various similar types of locks can be used, including a sliding lock, a detachable lock, magnetic or elastic members, a snap, a clasp, etc. As in the shown examples, the moveable locking device 60 is comprised of a horizontal surface 62 that can rotate together (see FIGS. 8-10) around a pivot point 63 so that the horizontal surface 62 of the moveable locking device 60 can be positioned underneath the hook 26 and catch 27 as best shown in FIG. 8, and/or even underneath the side wall portions 22a, 22f and/or stand-offs 28. In this way, the moveable locking device 60 inhibits or prevents the hook 26 from being lifted upwards from the catch 27, because the horizontal surface 62 is located underneath the catch 27, in the event of an inadvertent upwards movement of one of the side wall portions 22a, 22c, 22d, and 22f. For example, in an engaged state, the moveable locking device closes the recess of the inverted U-shaped hook to inhibit the hook from being lifted upwards from the catch, and in a disengaged state, the moveable locking device is rotated out of the way to permit the hook to be being lifted upwards from the catch. Optionally, the moveable locking device 60 can include an vertical surface 61 (FIG. 7) attached to or formed with the horizontal surface 62. The vertical surface 61 can act as a handle to facilitate movement of the moveable locking device 60, and may further act as a stop that abuts the outer surface of the adjacent side wall portion to indicate when the moveable locking device 60 in the fully closed (i.e., locked) position. If no vertical surface 61 is used, the horizontal surface 62 may include an extended portion that can act as a handle. Preferably, the moveable locking device 60 is attached to the body 20a or 20b at a location adjacent to the hook 26 that that is positioned to be selectively moveable underneath the hook 26. In this way, the inverted U-shaped hook 26 extends around an upper portion of the catch 27 (i.e., the upper three sides) while the moveable locking device 60 extends below a lower portion of the catch 27 (i.e., the lower side). Thus, the catch 27 is captured and non-removable from the hook 26 while the moveable locking device 60 is in the locked position.

Figure 9:
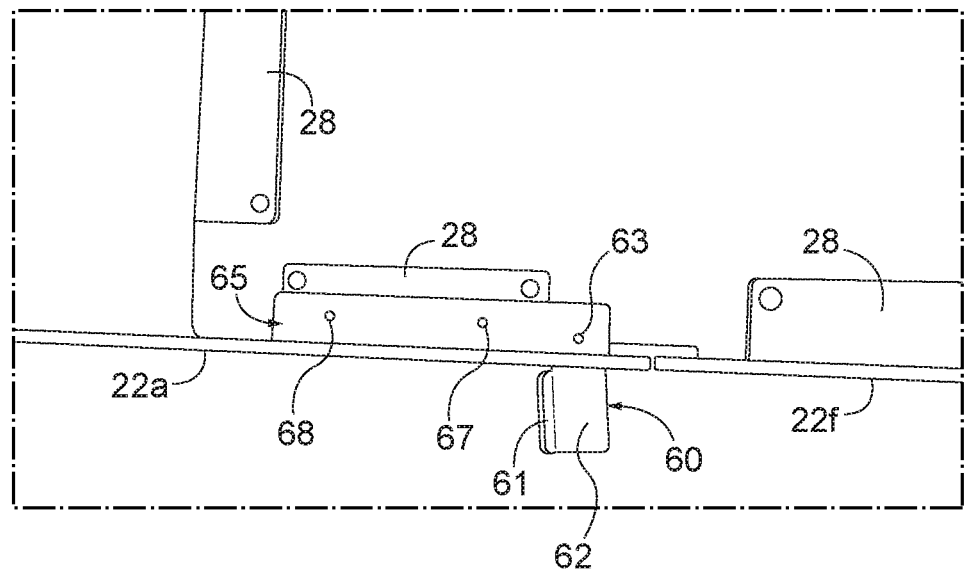
FIG. 9 shows a top view of the moveable locking device in the unlocked position of FIG. 7.
Figure 10:
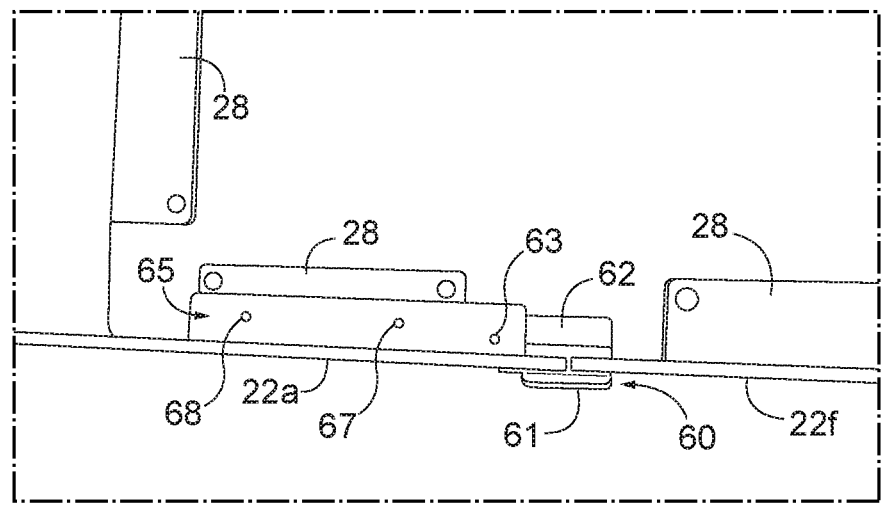
FIG. 10 shows a top view of the moveable locking device in the locked position of FIG. 8.
Figure 11:
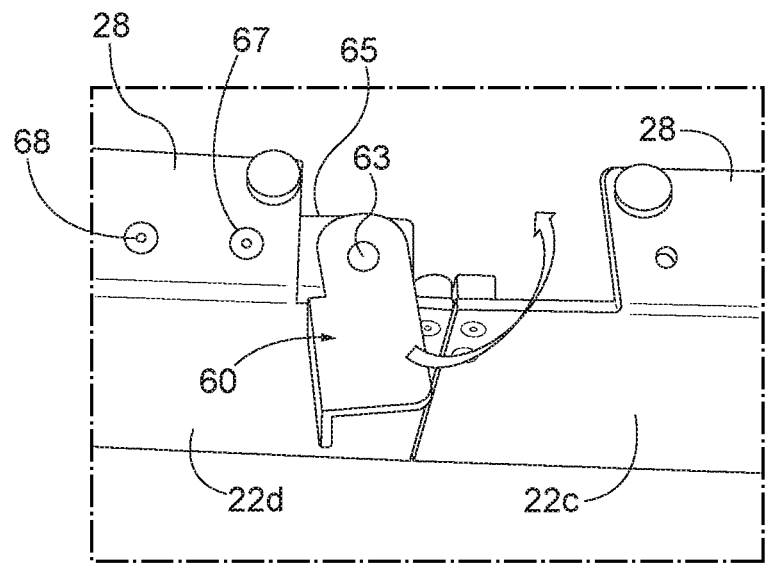
FIG. 11 shows a bottom view of the moveable locking device in the unlocked position of FIG. 7.
Figure 12:
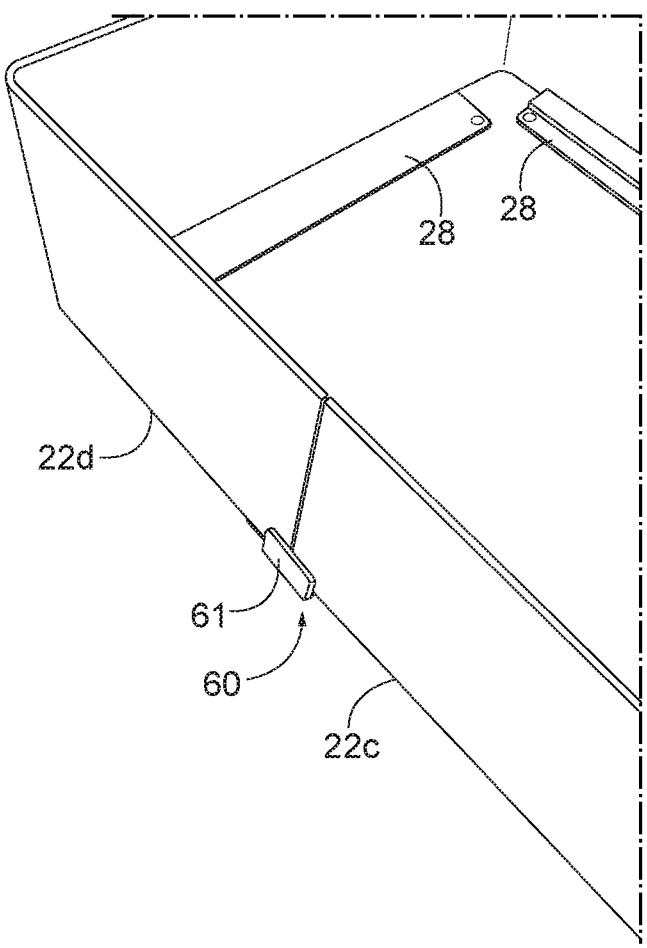
FIG. 12 shows a top perspective view of the moveable locking device in the locked position of FIG. 8.

The moveable locking device 60 can be attached variously to the body 20a or 20b. In one example, the moveable locking device 60 is shown to be attached (see FIGS. 8-10) to a rectangular-shaped support platform 65 by way of a rotatable hinge (e.g. rotatable pin, or other rotatable fastening device) that is inserted through the pivot point 63 of the support platform 65. Optionally, the support platform 65 can be removably connected (see FIGS. 9-10) to one of the inwardly projecting stand-offs 28 on the side wall portions 22a, 22c, 22d, and 22f by way of a removable fastener (e.g. screw, nut, bolt, etc.), for example at attachment point(s) 67 and 68. As shown in FIGS. 7, 9, and 11, the moveable locking device 60 is shown in an open position so that the vertical surface 61 and horizontal surface 62 are positioned perpendicularly to the side wall portions 22a and 22c (e.g., one on each side of the bodies 20a, 20b). To place the moveable locking device 60 into a closed (i.e. locked) position, the vertical surface 61 can be pressed inwards to rotate the moveable locking device 60 around the pivot point 63 so that the top of the horizontal surface 62 comes to a final resting position underneath the hook 26 and catch 27, as shown in FIGS. 8 and 10. This can further be indicated when the vertical surface 61 abuts the outer surface of the adjacent side wall portion to indicate when the moveable locking device 60 in the fully closed (i.e., locked) position.

As shown in the examples of FIGS. 7-11, the hook 26 and catch 27 can be removably or non-removably connected to the side wall portions 22a, 22c, 22d, and 22f by way of mechanical fasteners (e.g. hex screw, nut, bolt, rivet, etc.) that can be inserted through a plurality of pre-formed (e.g. punched, extruded, drilled, etc.) holes 66 (see FIG. 7) located at the bottom interior-facing edge of the said side wall portions. In this way, two hooks 26 can be positioned on either the same or opposite facing body 20a or 20b. Similarly, two catches 27 can also be located on either the same or opposite facing body 20a or 20b. Preferably, each body 20a, 20b includes one hook at one side, and one catch on the other side; thus, the use of two bodies 20a, 20b provides two hooks and two catches. Alternatively, one body 20a can include two hooks (one each side) while the other body 20b includes two corresponding catches (one each side). Utilizing a mechanical fastener to attach the hook 26 and catch 27 to the side wall portions 22a, 22c, 22d, and 22f, affords the manufacturer the benefit of producing one bill of material for bodies 20a and 20b. Optionally, the hook and catch 27 can be non-removable secured to the bodies 20a and 20b by adhesives, welding, non-removable fasteners, etc.

Figure 13:
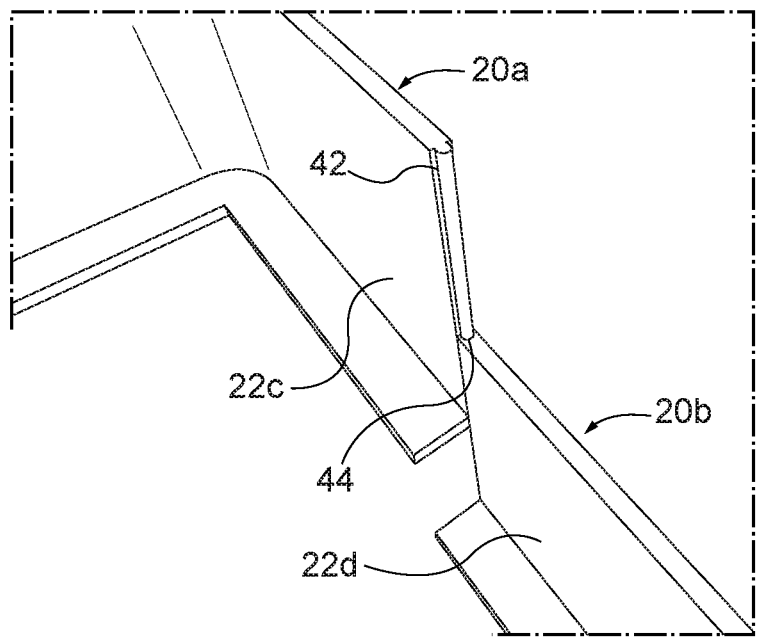
FIG. 13 shows another example of complimentary couplers suited to join bodies of the surround cladding protection device together.

Turning now to FIG. 13, in another example, the two bodies 20a and 20b of the surround cladding protection device 20 can be removably coupled together by complimentary couplers 24 that include a key 42 and slot 44. In this example, an integrally formed cylindrically-shaped key 42 extending outwards from side wall portion 22c of body 20a is vertically slid downwards into an open circular-shaped slot 44 integrally formed into an opposite side wall portion 22d of body 20b. To accommodate a vertical sliding motion, the circular-shaped slot 44 has an inside diameter that is dimensionally larger than the corresponding outside diameter of the cylindrically-shaped key 42. The key 42 and slot 44 could also be connected by a snap-fit arrangement. Although described as having a circular geometry, it is to be appreciated that various other shapes and geometries are contemplated.

Although not shown, the key 42 would also be featured on the other inwardly facing side wall portion 22f of body 20b. Likewise, the other inwardly facing side wall portion 22a of body 20a would also feature an open slot 44 for the purpose of slidably receiving a key 42. In this aspect, the design of bodies 20a and 20b can be based on the same engineering bill of material to minimize manufacturing costs. When the keys 42 are slid downwards into the slots 44 so that the top of side wall portions 22a-f are flush, the surround cladding protection device 20 is assembled and held in place around the pedestal base 34 by gravity.

Various other key 42 and slot 44 configurations are also contemplated. For instance (not shown), the key 42 could represent a single square-shaped key, or a plurality of square-shaped keys extending outwards from inwardly facing side wall portions 22c and 22f. In this example, the square-shaped key can then be horizontally slid into one open square-shaped receiving slot, or into a plurality of open square-shaped receiving slots integrally formed into inwardly facing side wall portions 22a and 22d.

The said receiving slots would be dimensioned so as to permit for slidable insertion of the square-shaped keys, but also provide for enough friction to inhibit an inadvertent horizontal separation of the two bodies 20a and 20b as the surround cladding protection device 20 is situated around the pedestal base 34. Alternatively, circles, curves, polygons, or other shaped keys could also be envisioned that correspond to open receiving slots of a similar shaped structure.

Figure 14:
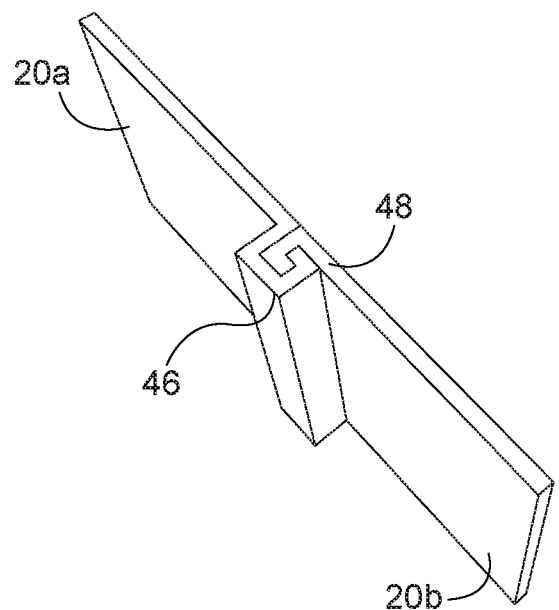
FIG. 14 shows yet another example of complimentary couplers suited to join bodies of the surround cladding protection device together.

Now referring to FIG. 14, an alternative complimentary couplers design is shown comprising two complimentary L-shaped securing elements 46 and 48 integrally formed onto inwardly facing side wall portions of bodies 20a and 20b. The two bodies 20a and 20b can be removably coupled together by vertically sliding the L-shaped securing element 46 extending inwards from body 20a into the slot that is formed by the L-shaped securing element 48 extending inwards from body 20b. As in the aforementioned key 42 and slot 44 coupling example, the L-shaped securing elements can be dimensioned so that the L-shaped slot formed by securing element 48, permits for a slidable motion between the two L-shaped securing elements 46 and 48. To assemble the surround cladding protection device 20 around the pedestal base 34, the L-shaped securing element 46 is vertically slid downwards until the top of side wall portions 22a-f are flush. As in the previous examples, the bodies 20a and 20b would be secured in place around the pedestal base 34 by gravity. As can be appreciated, the L-shaped securing element 46 can be situated on side wall portions 22c and 22f. Similarly, side wall portions 22a and 22d could also feature the L-shaped securing element 48 to maintain one engineering bill of material for bodies 20a and 20b.

Figure 15:
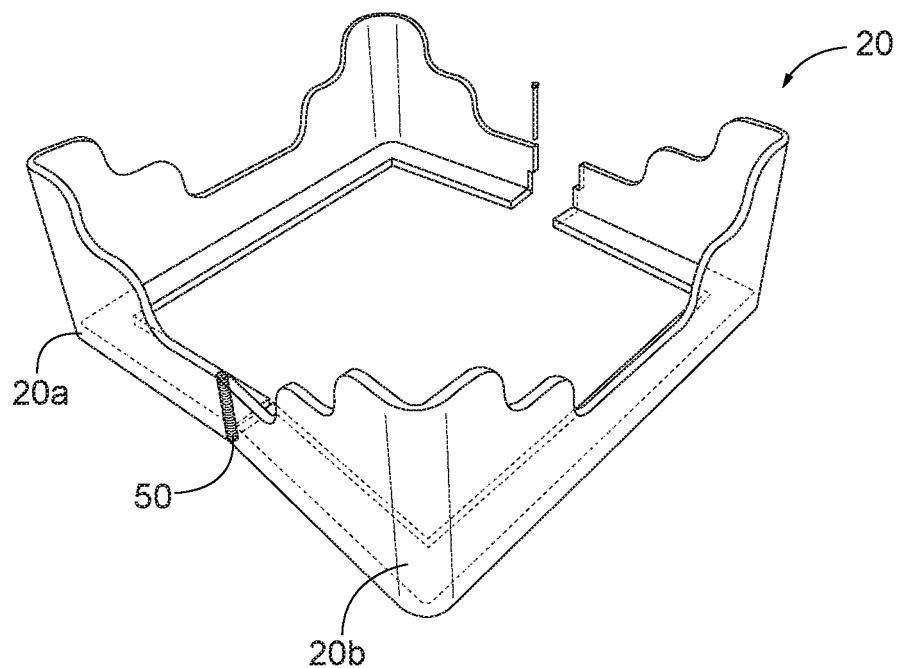
FIG. 15 illustrates a perspective view of another example of a surround cladding protection device.
Figure 16:
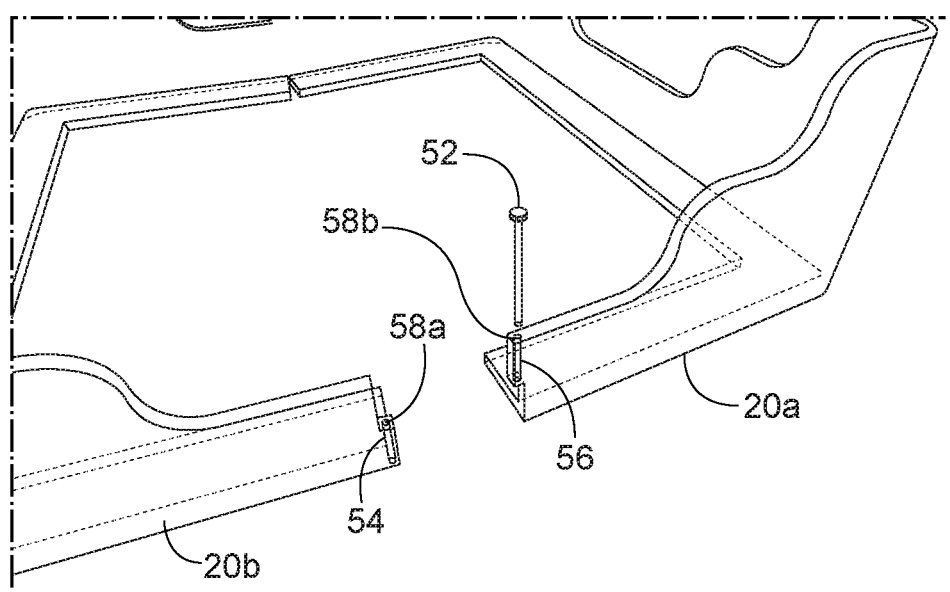
FIG. 16 illustrates an example of complimentary couplers that include a fastener design that joins bodies of a surround cladding protection device together.

In another example as shown in FIG. 15, the surround cladding protection device 20 can be comprised of two integrally formed pieces that can be symmetrically folded over upon a suitable hinge 50 (e.g. barrel hinge, butt hinge, piano hinge, etc.). Alternatively, a living hinge (not shown) could be utilized for a surround cladding protective device 20 comprised of elastically deformable material (e.g., plastic). In this embodiment, the two bodies 20a and 20b are folded over upon the hinge 50 and secured together (see FIG. 16) by complimentary couplers that include a removable fastener 52 (e.g. locking bolt, pin, screw, etc.) that is inserted into holes 58a and 58b that are pre-formed (e.g. punched, drilled, cored, extruded, etc.) into two inwardly facing members 54 and 56 extending inwards from bodies 20a and 20b. Various other clasps, snaps, interlocking mechanical structures, etc. can also be used.

As shown, the inwardly facing members 54 and 56 of the securing system are integrally formed onto bodies 20a and 20b. However, alternative variations could be envisioned such as where the inwardly facing members 54 and 56 are removably affixed onto the wall surface of bodies 20a and 20b by mechanical fasteners (e.g. nut, bolt, screw). In another example, the inwardly facing members could also be secured onto the wall surface of bodies 20a and 20b by way of a permanent setting adhesive.

The two members 54 and 56 of the securing system, which are shown to be rectangular-shaped, interconnect so that the underside of member 56 slides over the top surface of member 54 to complete the formation of a fourth wall of the surround cladding protection device 20. To secure the connection, the removable fastener 52 is inserted into holes 58a and 58b and is further held in place by gravity. However, the fastener could alternatively be screwed into place in the event a threaded fastener system is preferred. It could further be contemplated that member 56 has an elastically deformable lip that snaps into place over an upwardly protruding nub integrally formed onto the top surface of member 54.

Figure 17:
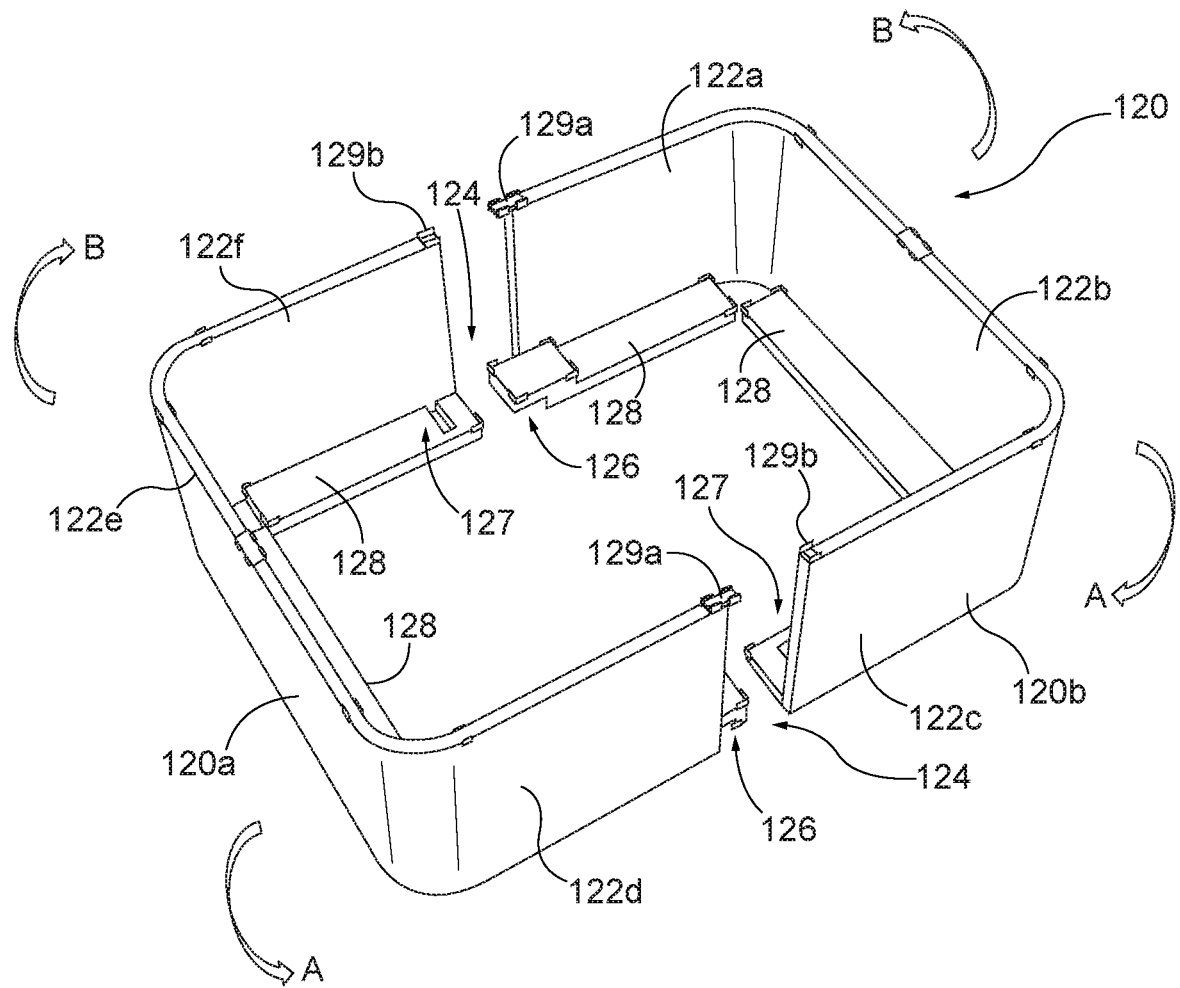
FIG. 17 illustrates another example surround cladding protection device, with the bodies separated apart.
Figure 18:
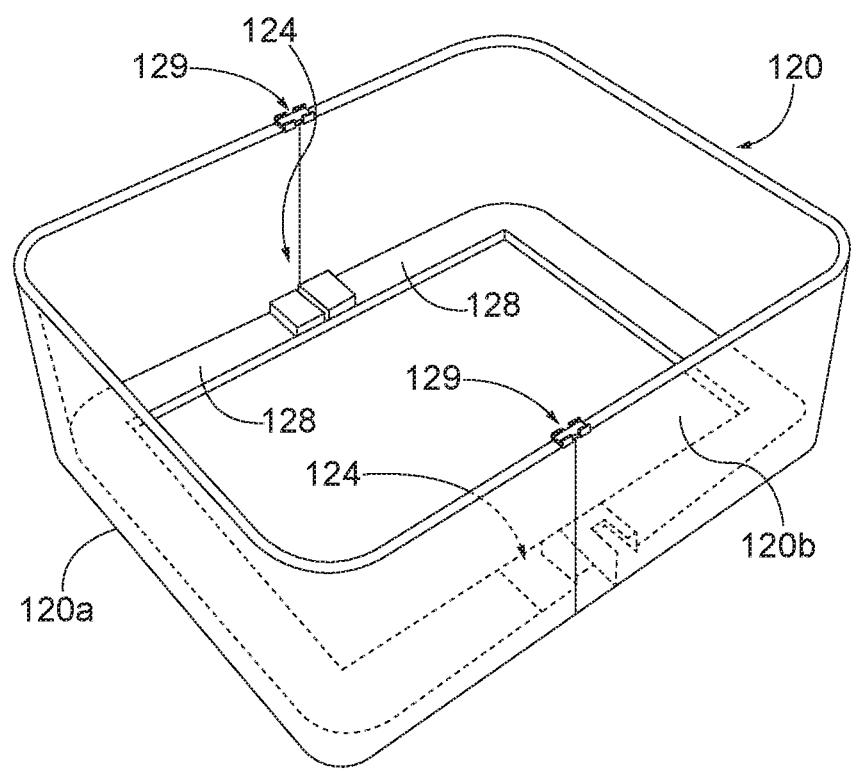
FIG. 18 illustrates the surround cladding protection device of FIG. 17 with the bodies secured together.

FIGS. 17-18 illustrate yet another example embodiment of a surround cladding protection device 120 that is formed of a pair of bodies 120a, 120b. FIG. 17 illustrates the bodies 120a, 120b separated apart, while FIG. 18 illustrates them connected together to form the completed surround cladding protection device 120. In the shown example, the two bodies 120a and 120b are presented as symmetrical halves featuring generally continuous side wall portions 122a-f of bodies 120a and 120b. Of course, various geometries and sizes are contemplated.

As before, a pair of complimentary couplers 124 can be used to secure the bodies 120a, 120b together. As shown, the complimentary couplers 124 comprise a male projection 126 and a female 127 recess that are sized and shaped to fit together when assembled. The male projection 126 may be an element that extends outwards from a base surface, or may even comprise a hook. FIG. 17 shows the male projection 126 and female recess 127 separated, while FIG. 18 shows the male projection 126 captured within the female recess 127. The complimentary couplers 124 can be attached variously to the side wall portions 122a-f of the bodies 120a and 120b. Preferably, the male projection 126 and female recess 127 are located on the interior surface of the side wall portions, although they could also be positioned on the outer walls (not shown) in another embodiment. As shown, the complimentary couplers 124 can also be attached to and/or integrally formed as part of a stand-off 128 on an interior side of the bodies 120a, 120b. For example, the male projection 126 can be removably or non-removably secured to a stand-off 128, and may extend a distance outwards therefrom. As shown in FIG. 17, the male projection 126 may be positioned to extend a distance past the terminal edge of the side wall that defines one of the bodies 120a or 120b. The female recess 127 can be formed as a blind hole or a through hole into/through the opposing stand-off 128 on the other of the of the bodies 120a or 120b. The male projection 126 can extend in a direction towards the female recess 127 so as to be readily fit together. In the shown example of FIG. 17, the male projection 126 can be oriented to extend downwards and the female recess 127 can likewise be open vertically upwards to receive the male projection 126 by gravity.

When the complimentary couplers 124 are engaged together, the bodies 120a, 120b are secured together to form the cladding protection device 20; conversely when the complimentary couplers 124 are disengaged from each other, the bodies 120a, 120b are unsecured and able to be separated. As shown in FIG. 18, to secure bodies 120a and 120b together around the pedestal base 34, the male projection 126 is seated into the female recess 127 and is secured in place by gravity. The male projection 126 and female recess 127 could also be retained together via clips, clasps, an interlocking structure, a tight tolerance or interference fit, or by other mechanical fasteners, etc. As shown in FIG. 17, in an embodiment where the male projection 126 and female recess 127 are parallel to their respective stand-offs 128 and extend towards each other, they may simply clip together when slid towards each other. However, if the male projection 126 and female recess 127 are made of a rigid material, there may be insufficient flex to permit a snap clip to occur. Instead, the bodies 120a, 120b may be rotated along a central transverse axis at a pivoted angle relative to each other, for example pivoted along the direction of arrows A in FIG. 17. Such a pivoted orientation permits sufficient clearance for the male projection 126 to be physically located above the female recess 127, whereupon counter-rotation along the direction of arrows B in FIG. 17 will cause the male projection 126 to be seated securely within the female recess 127.

The male projection 126 and the female recess 127 may stay in the engaged condition simply by gravity, or a secondary locking mechanism may be used. In one example, the male projection 126 and/or the female recess 127 may have a snap-fit geometry, such a detent-groove structure. Alternatively, the bodies 120a and/or 120b may include a secondary locking mechanism 129. In one example, the secondary locking mechanism 129 can include a pin 129a and corresponding hole 129b structure or other similar locking structure (e.g., a detent-groove structure, magnetic, elastic members, snap, clasp, hook and eye type clips, an interlocking structure, a tight tolerance or interference fit, other mechanical fasteners, etc.). As shown in FIG. 17, the secondary locking mechanism 129 can be located on a top surface of the side wall portions 122*a-f*, at a terminal edge of the bodies 120*a* and/or 120*b*. The secondary locking mechanism 129 can likewise be secured together by way of the pivoted rotation of the bodies 120*a*, 120*b*, and when engaged can help to maintain the male projection 126 and the female recess 127 in the engaged condition. It is further contemplated that the secondary locking mechanism 129 can likewise be used together with the previously-described hook 26 and catch 27 to ensure they remain secured together. In such an embodiment, the secondary locking mechanism 129 could be located in a similar position and function in a similar way.

It can be appreciated that each of the separate bodies 120*a* and 120*b* can be formed from a single design whereby each body 120*a* and 120*b* includes a male projection 126 and a female recess 127 to reduce the engineering bill of materials for bodies 120*a* and 120*b*. In this way, a single design could be manufactured, and the completed surround cladding protection device 120 can be formed by connecting the two bodies 120*a* and 120*b* together in a mirror arrangement. Alternatively, one body 120*a* can have two male protections 126 (one each side) while the other body 120*b* can have two corresponding female projections 127 (one each side).

Figure 19:
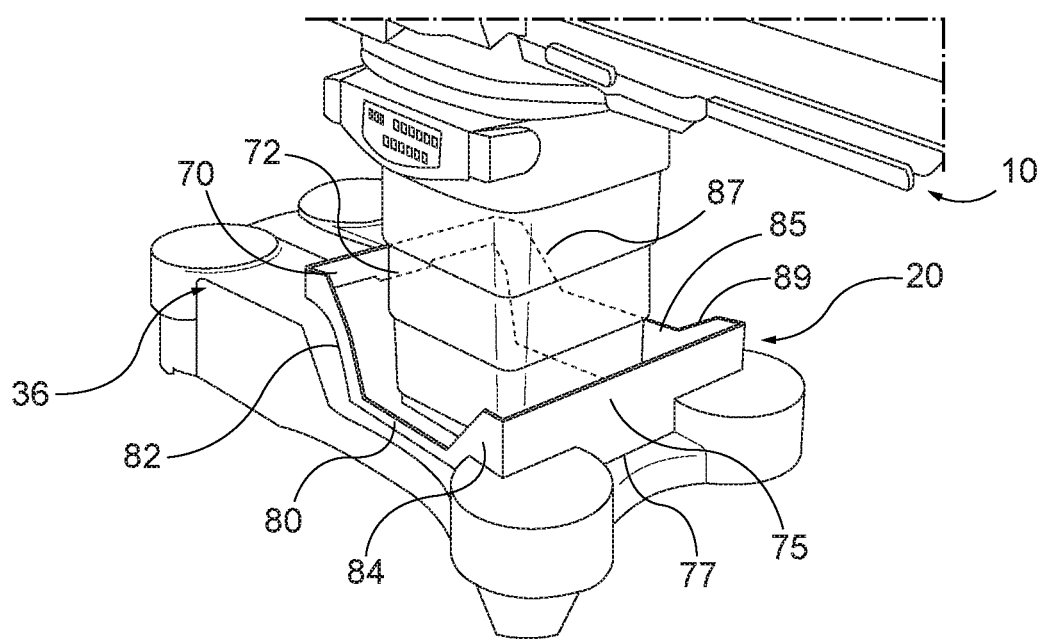
FIG. 19-20 illustrate yet another example of a surround cladding protection device that is installed upon an example operating room table.
Figure 20:
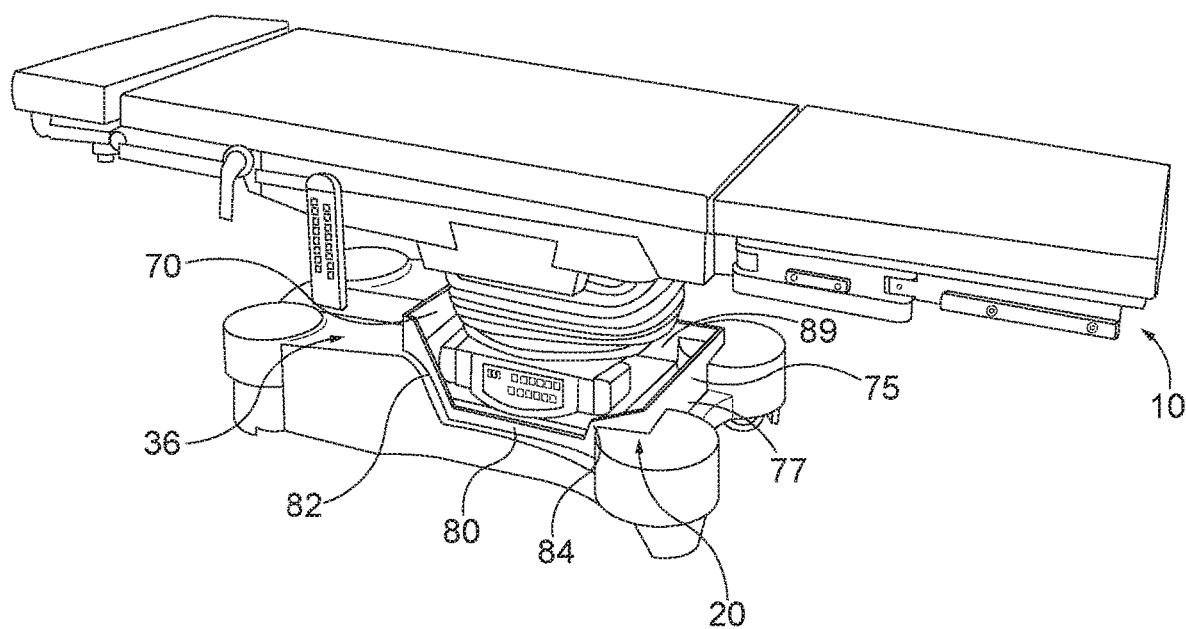

In another example (see FIGS. 19-20), the surround cladding protection device 20 can be designed to have side wall portions 70, 75, 80, and 85 that have varying dimensions and/or heights designed to accommodate multiple configurations and/or contours of surgical table base 36 designs. Although the table base 36 still has a generally horizontal orientation, there may be various angles, curves, etc. that break up an otherwise relatively flat surface. In this way, the dimensions and corresponding base positions of side wall portions 70 and 75 can be different from the dimensions and corresponding base positions of side wall portions 80 and 85 based on upwardly protruding risers 82, 84, 87, and 89 that are integrally formed onto the side wall portions 80 and 85 as shown.

Optionally, downwardly protruding tabs 72 and 77 can be integrally formed onto side wall portions 70 and 75 to fit within recesses of the surgical table base 36. As can be appreciated, the risers 82, 84, 87, and 89 and tabs 72, and 77 can be comprised of various sizes, shapes, and forms and can also be positioned at alternative locations corresponding to varying types of surgical table base 36 designs (e.g. a riser in the middle of a side wall portion, a tab at a corner location of the surround cladding protection device, etc.). Further yet, the risers 82, 84, 87, and 89 could also be designed (not shown) so that the base position of side wall portions 70 and 75 are located at a lower height than the base position of side wall portions 80 and 85. For example, the surround cladding protection device 20 can be form-fit to closely follow the contour of the surgical table base 36 or other portion of the table. The side walls can be arranged at various suitable angles to match or generally follow the shape and contour of the surgical table base 36.

In addition to protecting the cladding assembly 30 of the surgical table 10, the surround cladding protection device 20 minimizes contamination of the base surface 36 in embodiments where there are no fastening members required to be installed or adhered onto the base surface 36 that can serve to accumulate to debris or other bacterial matter. For example, when the projecting stand-offs 28 abut the outer perimeter of the operating room cladding assembly 30. In this respect, the surround cladding protection device can be quickly removed by decoupling the two bodies 20*a* and 20*b*, and then further cleaned with a surgical table disinfectant after removal.

In further addition to the above, a sterile material may cover the any or all of the cladding protection device 20. A removable sterile covering may be used, and the cladding protection device 20 can include structure to secure the sterile covering thereto during use.

As a further benefit, the physical shape of the surround cladding protection device 20, which corresponds to the perimeter shape of the cladding assembly 30, aesthetically complements the surgical table to promote continuity with respect to the industrial design of the surgical table.

The invention has been described with reference to the example embodiments described above. Modifications and alterations will occur to others upon a reading and understanding of this specification. Examples embodiments incorporating one or more aspects of the invention are intended to include all such modifications and alterations insofar as they come within the scope of this disclosure.

What is claimed is:

1. A cladding protection device for protecting a vertically extending height adjustment mechanism used to raise and lower the height of an operating room table relative to a horizontal table base, the cladding protection device comprising:
    a plurality of bodies seated upon said table base of said operating room table, each of said plurality of bodies comprising at least one side wall portion extending at least partially along a perimeter of said height adjustment mechanism;
    a complimentary coupler comprising a first coupler on one of said plurality of bodies and a second coupler on another of said plurality of bodies, such that when one of the first and second couplers is received into the other of the first and second couplers, the plurality of bodies form the cladding protection device; and
    a pivotable locking device being pivotably coupled to one of said plurality of bodies and being pivotable between a disengaged position allowing the first and second couplers to be disengaged from one another and the plurality of bodies to be separable from each other, and an engaged position pivoted towards the other of said plurality of bodies and in which withdrawal of the first coupler and the second coupler from one another and separation of the plurality of bodies from one another is prevented,
    wherein in an installed state the cladding protection device surrounds said perimeter of said height adjustment mechanism to thereby inhibit foreign objects from contacting said height adjustment mechanism.

2. The cladding protection device of claim 1, wherein the first and second couplers of the complimentary coupler comprise a U-shaped hook defining an open recess, and an elongated I-shaped catch that is sized and shaped to fit into the open recess of the U-shaped hook.

3. The cladding protection device of claim 2, wherein the hook and catch are each attached to a separate one of the plurality of bodies at opposing locations, and are located on an interior surface of the side wall portions of said plurality of bodies.

4. The cladding protection device of claim 2, wherein the hook is an inverted U-shaped hook, and wherein the hook and catch are engaged when the hook is seated onto the catch and held in place by gravity.

5. The cladding protection device of claim 1, wherein the pivotable locking device is engaged with another of said plurality of bodies only in the engaged position of the pivotable locking device.

6. The cladding protection device of claim 2, wherein the hook and the pivotable locking device are both attached to the same one of the plurality of bodies.

7. The cladding protection device of claim 1, further comprising a plurality of inwardly projecting stand-offs located in close proximity with said perimeter of said height adjustment mechanism to inhibit directional movement of the cladding protection device when in the installed state around said height adjustment mechanism.

8. The cladding protection device of claim 7, wherein each side wall portion of each of the plurality of bodies comprises at least one stand-off.

9. The cladding protection device of claim 1, wherein the plurality of bodies are maintained upon said table base by gravity without use of fasteners.

10. The cladding protection device of claim 1, wherein a pair of side wall portions of the cladding protection device define a corner, and the corner has an increased height with respect to a nominal height of the side wall portions.

11. A cladding protection device for protecting a vertically extending height adjustment mechanism used to raise and lower the height of an operating room table relative to a horizontal table base, the cladding protection device comprising:
a plurality of bodies seated upon said table base of said operating room table, each of said plurality of bodies comprising at least one side wall portion extending at least partially along a perimeter of said height adjustment mechanism,
wherein the plurality of bodies are adapted to be removably connected together to form the cladding protection device; and
a plurality of inwardly projecting stand-offs located in close proximity with said perimeter of said height adjustment mechanism to inhibit directional movement of the cladding protection device when in an installed state around said height adjustment mechanism, at least one sidewall of each of the plurality of bodies comprising at least one stand-off,
wherein in the installed state the cladding protection device surrounds said perimeter of said height adjustment mechanism to thereby inhibit foreign objects from contacting said height adjustment mechanism and separation of at least an adjacent pair of the plurality of bodies from one another is prevented by a pivotable locking device coupled to one body of the pair of the plurality of bodies that is pivotable towards the other body of the pair of the plurality of bodies to prevent said separation.

12. The cladding protection device of claim 11, wherein each side wall portion of each of the plurality of bodies comprises at least one stand-off attached thereto.

13. The cladding protection device of claim 12, wherein each stand-off has a length less than the respective side wall portion that it attached to.

14. The cladding protection device of claim 12, wherein each stand-off is integrally formed together with an associated side wall portion.

15. The cladding protection device of claim 11, wherein each stand-off is oriented parallel to said horizontal table base.

16. The cladding protection device of claim 11, wherein the plurality of inwardly projecting stand-offs are configured to be in abutment with said perimeter of said height adjustment mechanism when the cladding protection device is in an installed state around said height adjustment mechanism.

17. The cladding protection device of claim 11, wherein said perimeter of said height adjustment mechanism is defined by N walls, and wherein the cladding protection device comprises at least N side wall portions.

18. The cladding protection device of claim 11, further comprising a complimentary coupler comprising a first coupler on one of said plurality of bodies and a second coupler on another of said plurality of bodies, such that when the first and second couplers are engaged together the plurality of bodies form the cladding protection device, and when the first and second couplers are disengaged the plurality of bodies are separable from each other.

19. The cladding protection device of claim 18, wherein the first and second couplers of the complimentary coupler comprise an inverted U-shaped hook defining an open recess, and an elongated I-shaped catch that is sized and shaped to fit into the open recess of the inverted U-shaped hook.

20. A cladding protection device for protecting a vertically extending height adjustment mechanism used to raise and lower the height of an operating room table relative to a horizontal table base, the cladding protection device comprising:
a plurality of bodies seated upon said table base of said operating room table, each of said plurality of bodies comprising at least one side wall portion extending at least partially along a perimeter of said height adjustment mechanism; and
a complimentary coupler comprising a first coupler on one of said plurality of bodies and a second coupler on another of said plurality of bodies, such that when the first and second couplers are engaged together the plurality of bodies form the cladding protection device,
wherein in an installed state the cladding protection device surrounds said perimeter of said height adjustment mechanism to thereby inhibit foreign objects from contacting said height adjustment mechanism, and
wherein said complimentary coupler is configured to be maintained at said table base around a lower-most perimeter of said height adjustment mechanism during movement of said height adjustment mechanism and is outwardly spaced from vertically-translating elements of the vertically extending height adjustment mechanism.

* * * * *